United States Patent [19]
Deardon et al.

[11] Patent Number: 6,083,001
[45] Date of Patent: Jul. 4, 2000

[54] APPARATUS AND METHOD FOR PARTICLE FEEDING BY PRESSURE REGULATION

[75] Inventors: Joe D. Deardon; Gregory S. Dollard, both of San Diego, Calif.; Geoffery L. Davis, Albany, Oreg.; Albert L. French, Lebanon, Oreg.; V. Kim Kutsch, Albany, Oreg.

[73] Assignee: Kreativ, Inc., San Diego, Calif.

[21] Appl. No.: 09/172,327

[22] Filed: Oct. 13, 1998

[51] Int. Cl.[7] .................................................. A61C 3/02
[52] U.S. Cl. .............................................. 433/88; 51/307
[58] Field of Search ...................... 433/88, 101; 51/307; 451/38, 78, 90, 456, 99, 39, 7, 101

[56] References Cited

U.S. PATENT DOCUMENTS

| | | | |
|---|---|---|---|
| 2,696,049 | 12/1954 | Black | 32/58 |
| 3,267,615 | 8/1966 | Moore | 51/5 |
| 3,834,082 | 9/1974 | Grudzinski | 51/12 |
| 3,852,918 | 12/1974 | Black | 451/38 |
| 4,038,786 | 8/1977 | Fong | 51/320 |
| 4,630,410 | 12/1986 | Cavada et al. | 51/410 |
| 4,709,515 | 12/1987 | Copeland et al. | 51/436 |
| 4,878,320 | 11/1989 | Woodson | 51/320 |
| 5,065,551 | 11/1991 | Fraser | 51/410 |
| 5,195,280 | 3/1993 | Nicholson et al. | 81/436 |
| 5,230,185 | 7/1993 | Kirschner et al. | 51/410 |
| 5,239,788 | 8/1993 | Woodson | 51/436 |
| 5,312,251 | 5/1994 | Jackson | 433/88 |
| 5,330,354 | 7/1994 | Gallant | 433/88 |
| 5,367,840 | 11/1994 | West | 451/78 |
| 5,407,379 | 4/1995 | Shank et al. | 451/99 |
| 5,525,058 | 6/1996 | Gallant et al. | 433/88 |
| 5,531,634 | 7/1996 | Schott | 451/39 |
| 5,556,325 | 9/1996 | Shank et al. | 451/101 |
| 5,605,497 | 2/1997 | Pickard | 451/90 |
| 5,618,177 | 4/1997 | Abbott | 433/88 |
| 5,718,581 | 2/1998 | Fernwood et al. | 433/88 |
| 5,752,829 | 5/1998 | Goldsmith et al. | 433/88 |

*Primary Examiner*—Gene Mancene
*Assistant Examiner*—Pedro Philogene
*Attorney, Agent, or Firm*—Lori M. Friedman

[57] ABSTRACT

The invention enables accurate control of particle flow with regard to feeding abrasive material to a surface. The unit does not employ a vibrator and may be used to remove undesired material from a surface. A particular application is in a dental air abrasion unit for both cleaning and cutting tooth surfaces. When used in an air abrasion dental instrument, the abrasive material is stored in a container which is separated from a mixing chamber by an orifice member. The flow of particles is electronically controlled by the differential in pressure in the container section above the particle level and the pressure below an orifice member in a mixing chamber. The resulting particle flow to the surface is substantially linear and less erratic than that of prior air abrasion instruments.

44 Claims, 10 Drawing Sheets

Comparative Figure A
(Prior Art)
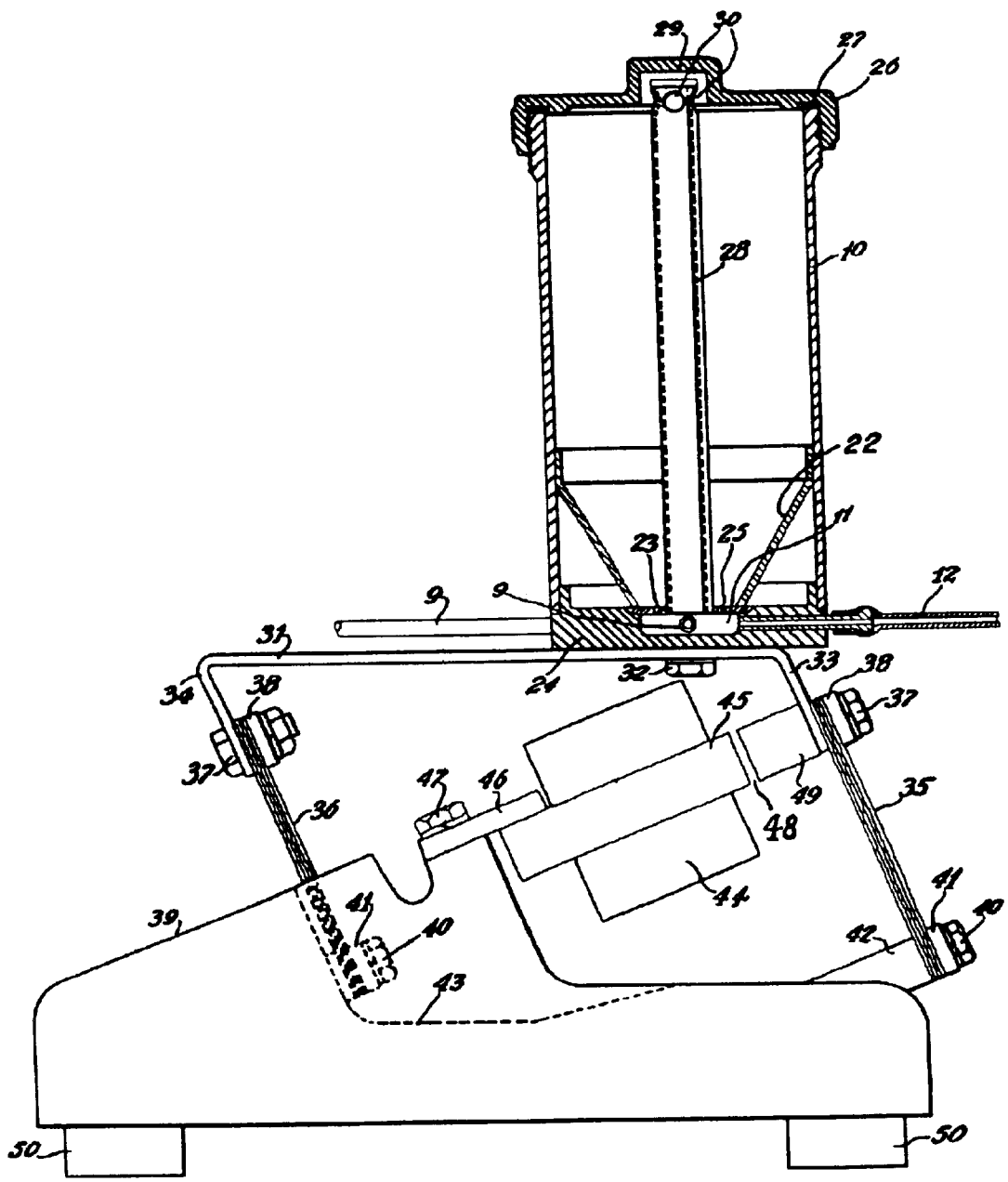

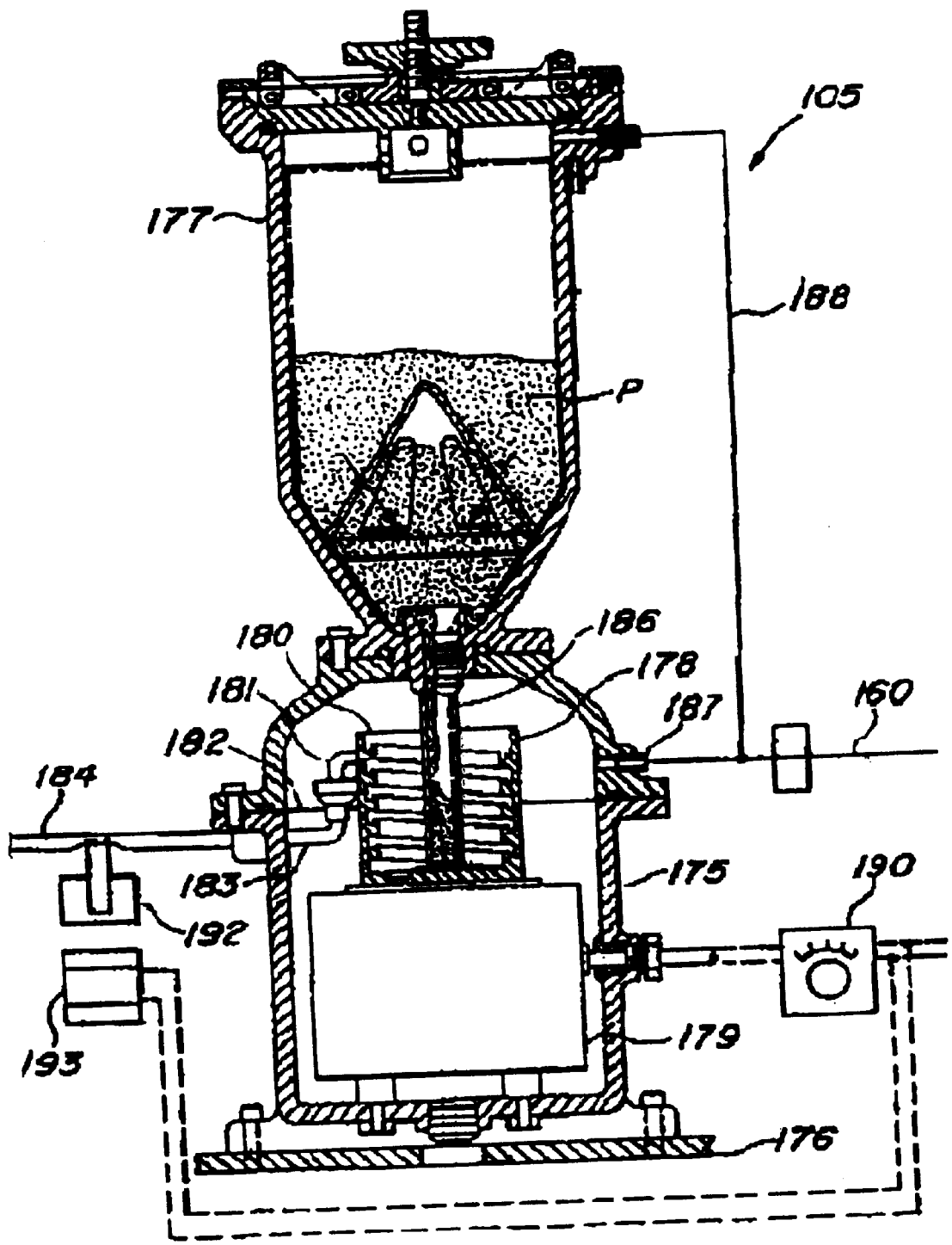
Comparative Figure B
(Prior Art)

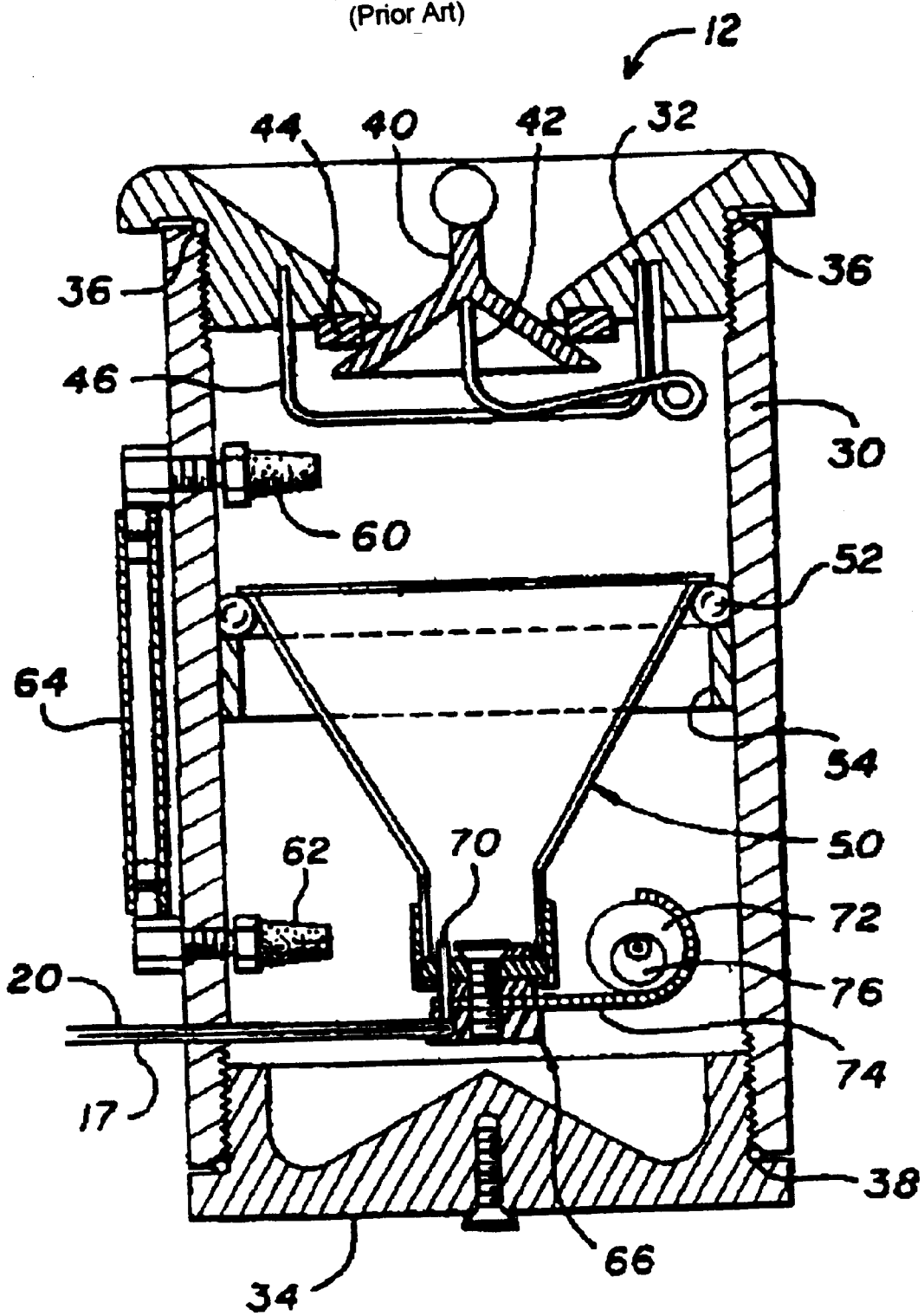
Comparative Figure C
(Prior Art)

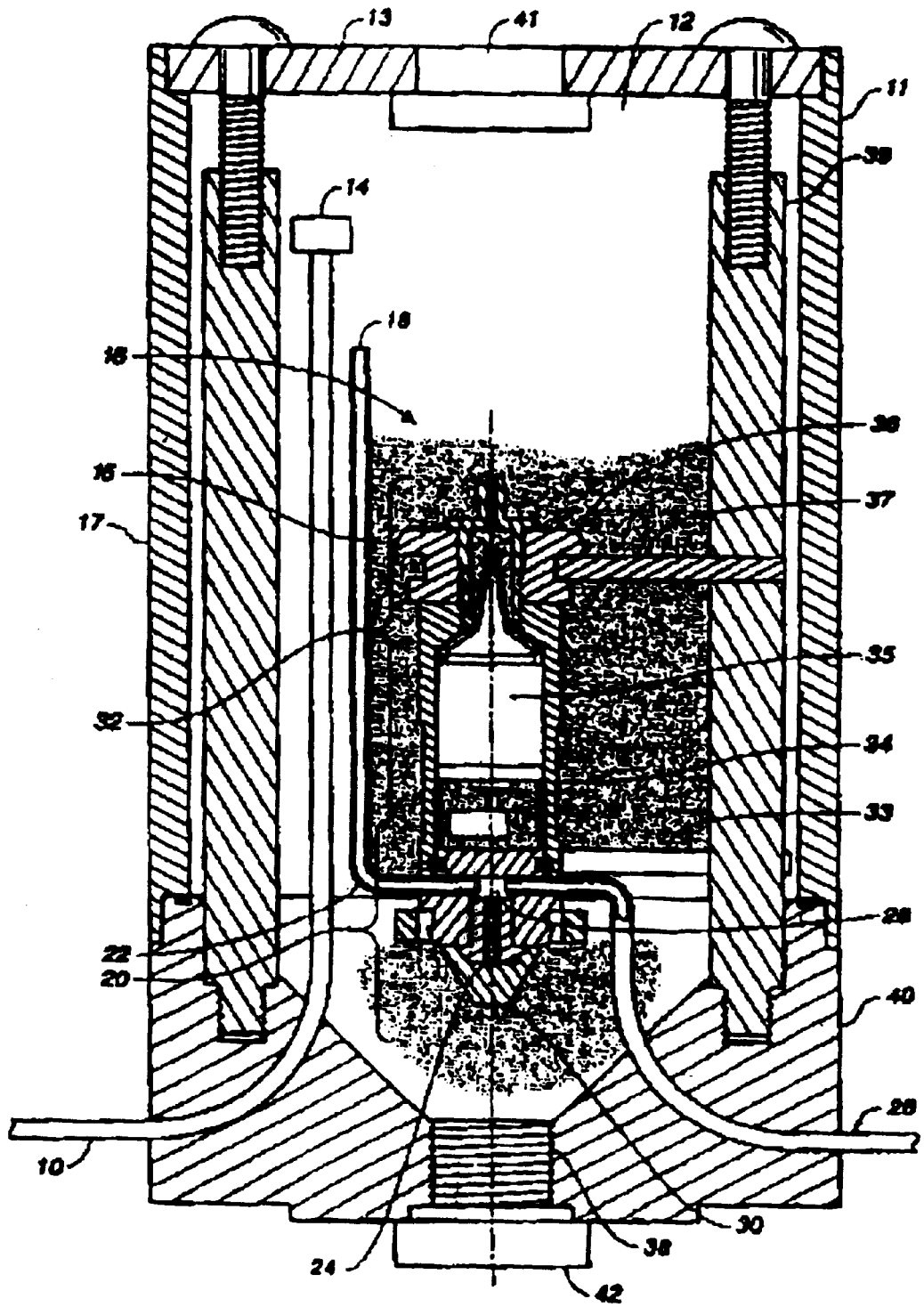
Comparative Figure D
(Prior Art)
US Patent 5,718,581

APPARATUS AND METHOD FOR PARTICLE FEEDING BY PRESSURE REGULATION

BACKGROUND OF THE INVENTION

1. Field of the Invention

The present invention relates to a method of feeding a stream of particles under pressure. Specifically, the stream may be comprised of abrasive particles which are fed to remove unwanted material from a surface. More specifically, a preferred use of the stream is the removal of undesirable material, such as decay or stains, from teeth in an air abrasion dental instrument.

2. Background of the Invention

Air abrasion instruments have been available for use by dentists for treating patients with an abrasive-laden fluid stream for many years. Among the advantages realized in air abrasion dentistry are increased patient comfort, alleviation of patient anxiety, decreased use of anesthesia, increase of dentists' productivity, and decreased costs to both patients and dentists.

This dental technique uses abrasive-laden streams which carry abrasive particles and a carrier gas. The stream is directed onto the patient's teeth for removal of decay, preparing the teeth to receive fillings, prophylactic treatment, and the like. Such air abrasion instruments provide advantages over conventional dental drills. These include eliminating the heat, noise, and vibration produced by conventional high-speed drills. Also lessened is the need for anesthesia as well as the need to cool the drill with fluid.

The use of directing a fluid stream of abrasive particles to the teeth to perform dentistry is known in the dental art. The general technique of treating teeth using such abrasive can be traced back to the 1950's and the work of Dr. Robert Black in U.S. Pat. No. 2,696,049. Some details of the feed system of Dr. Black's patent are described and presented in Comparative Figure A.

In '049, the abrasive particles were vibrated to effect their delivery from the storage compartment to the mixing chamber. The particles were kept in a constant state of motion. An improvement to the mixing system described in the Black patent was improved upon by others desiring to improve control of the flow of abrasive particles used in air abrasion dentistry.

One such improvement is recited in Ser. No. 08/975,438 filed on Nov. 21, 1997 and likewise assigned to Kreativ, Inc. This system, although equipped with such features as microprocessor and remote controls, had not greatly altered the particle feed system introduced by Dr. Black in '049. The aforementioned Kreativ patent application describes a unit which is equipped with a vibrator. The pressure in the container holding the particles varies as the dentist selects different operating pressures. The abrasive particles are gravity fed in the pending Kreativ application Another feed system for an air abrasion dental device is described in U.S. Pat. No. 5,525,058 to Gallant et al. Gallant utilizes a closed loop regulator to control air pressure. Their system operates with a plurality of servo valves which continuously monitor the output pressure and re-adjust the pressure control if the output is too high or too low. Specific features of this technology are presented and described as Comparative Figure B.

The '058 patent employs a vibrator and does not use gravity feed, as do the systems described above by Black and in the previously mentioned pending Kreativ application. The '058 feed system operates on a pressure principle with a mixture of particles and air being forced upward under pressure with vibrational activity, against gravity, through helical means.

Another invention concerned with the delivery of abrasive powder to a hand-held dental tool for air abrasive dental treatment is taught by Abbott in U.S. Pat. No. 5,618,177. The particle feed system of '177 uses both gravity feed and oscillation in its arrangement for feeding pressurized particulate material. The '177 feeder system employs a vibrator to vibrate the bottom of a hopper where abrasive particles are stored. The vibrator applies oscillatory forces and torques to the bottom portion of the hopper causing the powder in the hopper to fluidise and circulate within the hopper and across the inlet orifice. Details of the '177 patent may be seen in Comparative Figure C.

Still another method and apparatus for an air abrasive dental unit is disclosed in U.S. Pat. No. 5,718,581 to Fernwood et al. The apparatus disclosed therein utilizes an internal vibrator motor with vibration transmitters which transmit the vibrations throughout the jar containing abrasive In the '581 patent, the vibrator assembly in combination with the vibration transmitter maintains the favorable flow of particles under gravity feed. The particle feed system of '581 uses both gravity feed and oscillation in its arrangement for feeding pressurized particulate material. This system is illustrated in Comparative Figure D.

Prior to the instant invention, the feed systems of air abrasion dental instruments employed vibrators as part of their particle feed systems. Another feature common to the prior art systems is equalization means to equalize pressure in various parts of the unit. The particle flow of the prior art systems are not linear, have undesirable bursts of abrasive particles, and have less controllable particle feed streams.

Although linear flow is a desirable feature of air abrasion dentistry, it was not accomplished by the prior art systems. Linear particle flow, and other objects of the present invention, will be clarified shortly.

SUMMARY OF THE INVENTION

A first object of this invention is to illustrate a particle feed system that provides a linear flow of abrasive particles to a surface for removal of unwanted material from that surface. Such abrasive products are used in dentistry to prepare teeth for various dental treatments, such as removal of decay, prophylactics, stain removal, and the like. It is a further object of this invention to demonstrate a particle feeding device with a substantially vibration-free pressure differential feed system that enables the delivery of a linear flow of abrasive particles over a range of air pressures, particle flow rates, and particle sizes.

A further object of this invention is to demonstrate the use of the particle feeding device in air abrasive dental instruments with a substantially vibration-free pressure differential feed system. By controlling the difference in pressure between the area above the particle level in the particle container and below the orifice member in the mixing chamber, the particle flow rate out of the mixing chamber to the air abrasion handpiece is accurately controlled.

It is a further object to provide methods for performing various dental procedures which benefit from the linear, more regulated flow of abrasive particles to the teeth.

The resulting linear flow of abrasive results in less abrasive particle waste and increased efficiency of the dentist. The linear, more controllable particle feed allows lower pressures to be used for most dental procedures. Lower pressures correlate with less pain for the patient as well as greater control for the dentist.

The pressure equalization means and vibrator, present in many prior art air abrasion dental units, are eliminated in the instant invention. Elimination of these parts reduces both cost of materials and ease of manufacture for the producer as well as ease of use for the dental practitioner.

The particle feed system of this invention may be realized in a low cost, basic air abrasion dental instrument. Or, the particle feed system of this invention may incorporate features which may be used in an advanced, high-end unit with many options provided by microprocessor control. The high-end dental instrument, equipped with a microprocessor, optimizes particle flow for each pressure setting and nozzle tip selection.

The diagrams, description and claims which follow will point out and patently distinguish the instant particle feed system from those of the prior art.

DESCRIPTION OF THE FIGURES AND COMPARATIVE FIGURES OF THIS INVENTION

Figure 1:
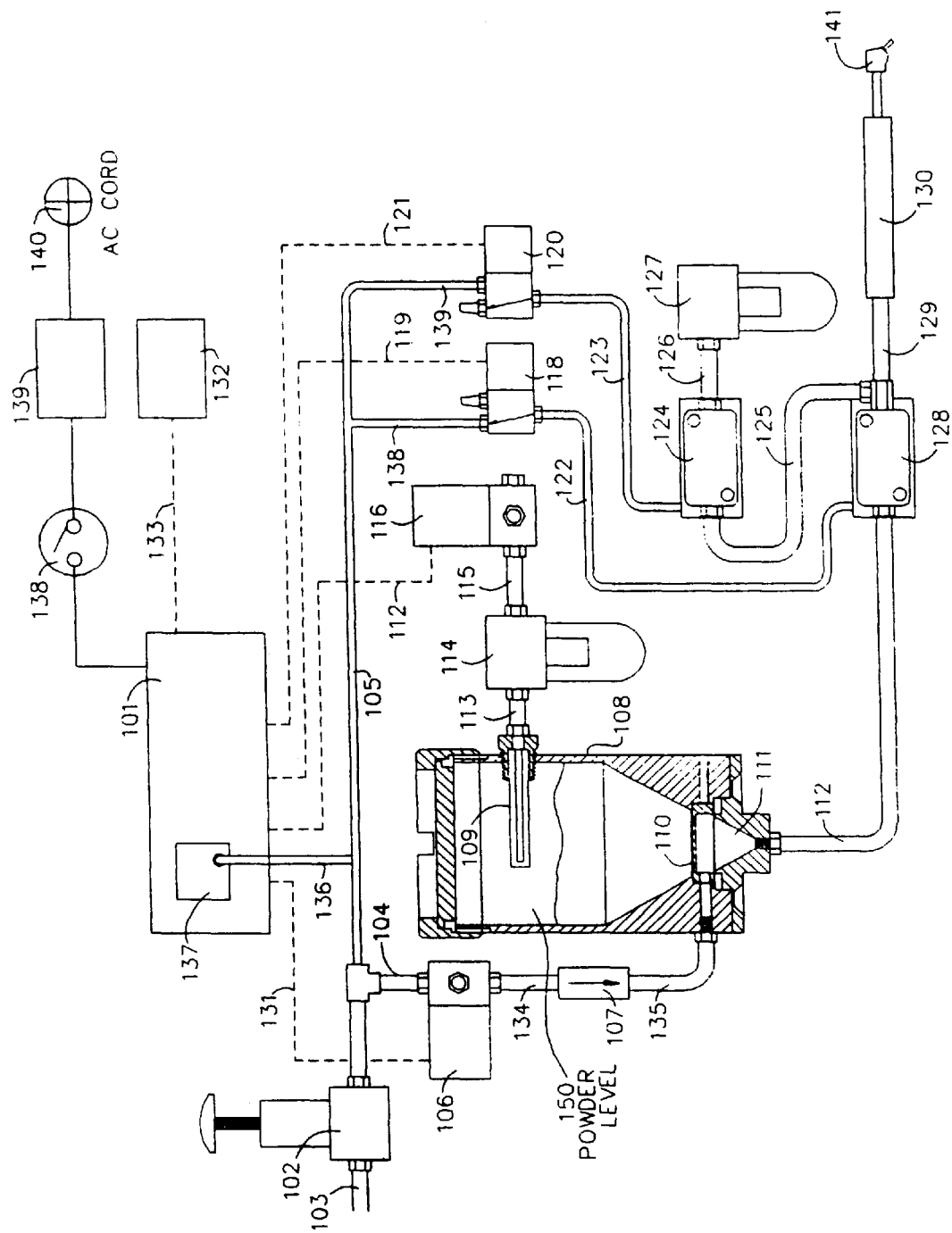
FIG. 1 is an operational diagram of the particle feed system of the invention.

Note that the figures of the instant invention picture pneumatic paths as solid lines. In contrast, electrical paths are pictured as dashed lines.

Comparative Figure A depicts the vibrator and particle feed system of U.S. Pat. No. 2,696,049 (prior art).

Comparative Figure B illustrates the vibratory feed system for an air abrasion dental systems from U.S. Pat. No. 5,525,058 (prior art).

Comparative Figure C from U.S. Pat. No. 5,618,177 (prior art) illustrates the arrangement for feeding pressurized particulate material from a storage member to a handpiece for performing air abrasion dentistry.

Comparative Figure D from U.S. Pat. No. 5,718,581 (prior art) illustrates the arrangement for feeding pressurized particulate material from a storage member to a handpiece for performing air abrasion dentistry.

DETAILED DESCRIPTION OF THE PREFERRED EMBODIMENTS OF THE INVENTION

The instant invention illustrates a particle feed system that uses synchronized pulsing to deliver linear streams of abrasive particles. Although useful in a variety of industries, preferred embodiments illustrated herein relate to providing air abrasion dental instruments that deliver linear, even flow of abrasive particles to the teeth. This feed system allows the dental practitioner increased control of the flow of abrasive stream of particles. In this invention, the terms 'powder' and 'particle(s)' are used interchangeably in describing abrasive material in particulate form.

In this invention, linear particle flow will mean that particle output varies in direct proportion to the beam intensity set by the practitioner using the instrument. Beam intensity is defined herein as the amount of abrasive material in the particle stream. The linear particle flow of this invention allows the user more precise control of the instrument's cutting ability at lower pressures.

Air abrasion dentistry uses abrasive-laden gas streams which carry a mixture of abrasive particles and carrier gas. Among the choices of gasses that may be used are air, nitrogen, and carbon dioxide. A preferred gas stream is dry air. The stream is directed onto the patient's teeth through a nozzle attached to a handpiece for removal of decay, preparing the teeth to receive fillings, prophylactic treatment, and the like. It is to be understood that in the following description, when air is used as the gas it may be substituted with nitrogen, carbon dioxide, or other non-flammable, non-hazardous gasses.

Abrasive materials that may be used in the dental processes discussed herein include sodium bicarbonate, urea, dolomite, aluminum oxide, and the like. An often used and preferred abrasive is aluminum oxide. Aluminum oxide, or alumina, used for cutting dental surfaces in air abrasion may be in particle size ranging from about 27 to about 50 microns in size. A preferred size of aluminum oxide is 27.5 microns and is available from Kreativ, Inc. as GammaPure™ (patent pending). For dental prophylactics, a preferred abrasive is sodium bicarbonate.

The particle feed system of the instant invention utilizes abrasive particles of substantially uniform particle size. The unit has a limited number of parts, allowing for simplified and less expensive manufacture and maintenance. Additionally, the device is self-cleaning since air flows in both directions through the orifice holes in the mixing chamber.

FIRST PREFERRED EMBODIMENT: PARTICLE FEED SYSTEM

FIG. 1 illustrates the operational diagram of the particle feed system of the invention. As schematically described therein, air is supplied to the unit via air line 103 by an external source (not shown). When power is turned on via toggle switch 138 and air is supplied at 103, the desired pressure is set by the hand adjusted pressure regulator 102 or may be automatically adjusted by a microprocessor in the electronic control module 101. This setting is detected by the pressure transducer 137 via paths 105 and 136.

FIG. 1 depicts the container member 108, porous filter 109, particle level 150, orifice member 110, and mixing chamber 111. These features may be referred to as the "container section" of the powder feed apparatus of the instant invention. The container section holds a mass of loosely packed abrasive particles in the container 108. When ready to be fed, the particles flow from the container member 108 to the mixing chamber 111 through the orifice member 110. The mixing chamber 111 is separated from the abrasive particles at level 150 stored in container 108 by an orifice member 110. When particle flow is desired, the differential in pressure between the level of particles in the container 108 and below the orifice member 110 is synchronized with the opening and closing of certain valve members, as described in detail below, causing flow of abrasive particles to a handpiece 130. This pressure differential may range from zero to about 100 psi.

Figure 4:
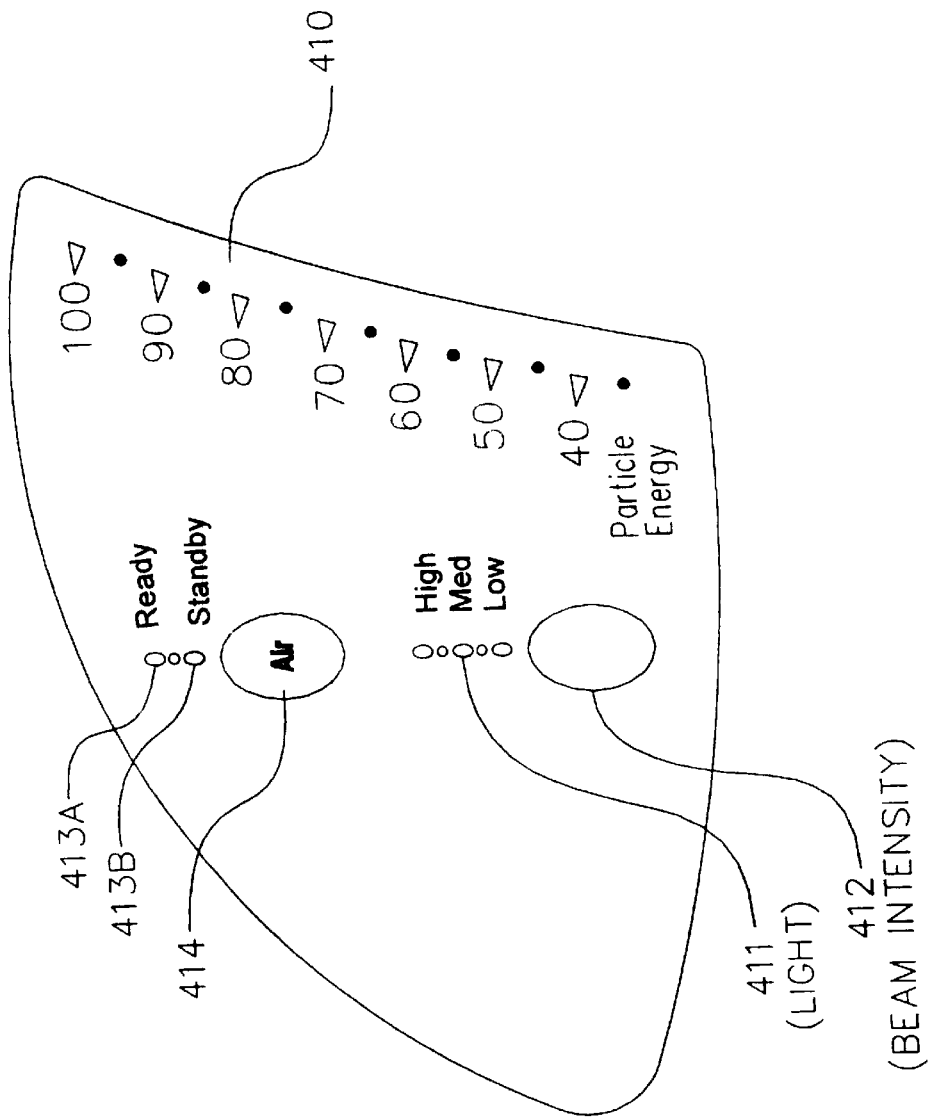
FIG. 4 depicts the control panel of the feed system of the present invention embodied in a basic air abrasion dental unit.
Figure 5:
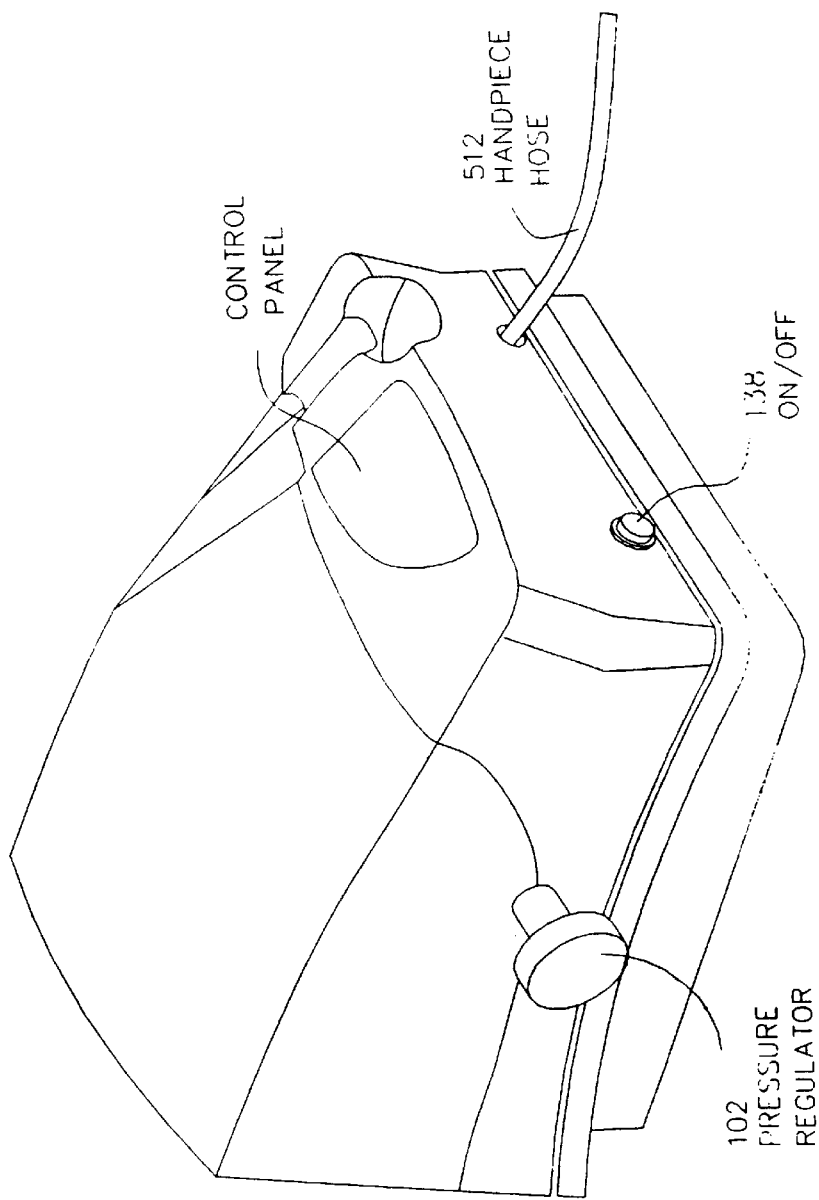
FIG. 5 shows the body of the basic air abrasion dental instrument utilizing the instant particle feed system.

When power is on, the electronic module 101 defaults to "Standby". The electronic control module 101 controls solenoid 118, allowing air flow from path 105 to path 122. This causes abrasive pinch valve 128 to close, stopping fluid flow to the handpiece 130. The dental practitioner activates the unit into the "Ready" mode by pushing button 414, as shown in FIG. 4. This causes solenoid valve 106 to open and pressurize the system.

The user then activates particle flow by depressing activation switch 132. This activation sends a signal via line 133 to the electronic control module 101. The control electronics then begin the following series of operations:

1. Solenoid valve 120 is controlled by the electronic control module 101 through path 121. This allows air to flow from path 105 to path 123. It also pressurizes pinch valve 124. Pinch valve 124 closes air paths 125 and 126.
2. Solenoid valve 118 is then electronically controlled by 101 through path 119. This allows abrasive pinch valve 128 to open and close according to the unit's pulse timing characteristics. When abrasive pinch valve 128 is to be closed, solenoid valve 118 allows air flow from path 105 to path 122. When abrasive pinch valve 128 is to be opened, solenoid valve 118 depressurizes abrasive pinch valve 128 through path 122 and exhaust muffler 160.
3. As abrasive pinch valve 128 is opened, particles are drawn out of container member 108 through orifice member 110 and combined with the gas stream in mixing chamber 111. The gas that is combined with the particles from path 134 through one-way check valve 107 through path 135 flows through path 112 through abrasive pinch valve 128. The particles and air mixture then continues to flow to the handpiece 130 continuing to nozzle means 141 via path 129.
4. When the activation switch 132 is released, abrasive pinch valve 128 closes and pinch valve 124 opens to relieve back pressure in path 129 and handpiece 130. In order to open pinch valve 124, pressure is released from pinch valve 124 through path 123 and exhaust muffler 161. The back pressure flows in path 129 through path 125 through pinch valve 124, through path 126 and into the exhaust chamber 127. By relieving the back pressure through these paths, the particle flow through handpiece 130 and nozzle 141 stops immediately.
5. When the activation switch 132 is pushed, abrasive pinch valve 128 opens and closes about three times per second. Each of these open-close sequences draws a controlled amount of abrasive material out of the container member 108. In order to control the different amounts of particle flow, pressure is released off the top of the container member 108 through porous filter 109, path 113, catch filter 114, path 115, and solenoid valve 116. Solenoid valve 116 relieves pressure from the container member above particle level 150. It opens synchronously with abrasive pinch valve 128. The amount of time valve 116 is open determines the amount of particle flow.

Figure 2:
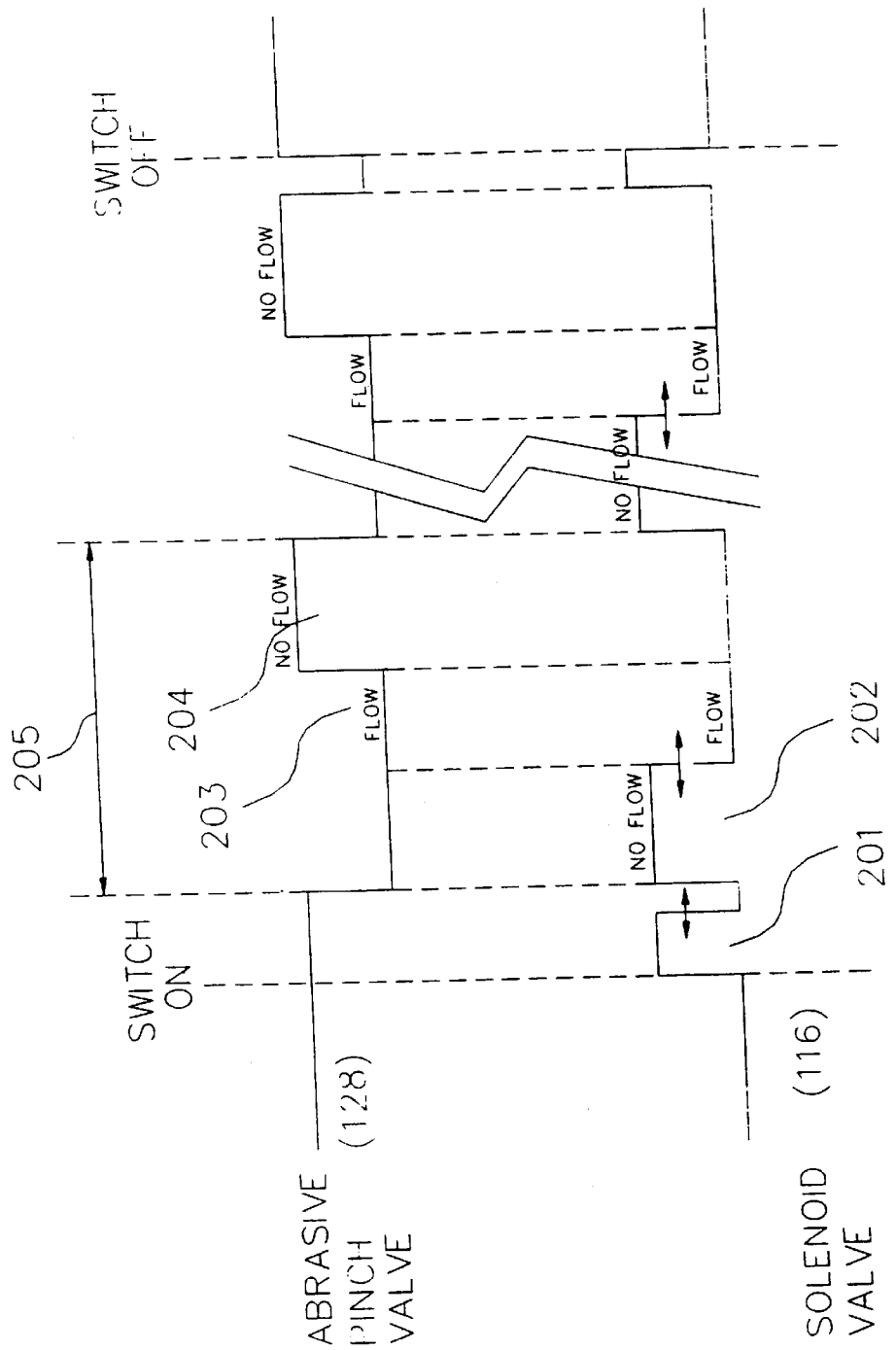
FIG. 2 is the timing diagram of the control valves and the activation switch positions (ON/OFF) of the particle feed system of the invention.

Further details of the timing sequences of the particle feed system of the present invention are shown in FIG. 2, which shows the timing of the opening and closing of abrasive pinch valve 128 and solenoid valve 116. This timing sequence starts when the activation switch is pushed, and time 201 is used to minimize initial particle bursts experienced in prior air abrasion dental instruments. Timing 201 only happens once after the activation switch is pushed and will not happen again until the activation switch is released and pushed again. Time 201 indicates that Solenoid valve 116 receives a signal via 112 from the electronic control module 101 to open for the initial burst duration time. The initial burst duration time 201 relieves pressure from the top of the particle level 150 through filters 109 and 114. The initial burst duration reduces pressure above the particle level 150 to be less than the pressure in the mixing chamber 111. This pressure differential helps minimize initial particle bursts through handpiece 130.

When time 201 ends, times 202, 203, and 204 start repeating, and continue to repeat until the activation switch is released. The repeating timing sequence is represented as time 205. Time 203 indicates the time abrasive pinch valve 128 is opened, time 204 indicates the time the abrasive pinch valve 128 is closed. Time 202 indicates the time pressure is being released out of the top of the canister by solenoid valve 116.

When abrasive pinch valve 128 opens for time 203, valve 116 also opens for a period of time 202 that is less than or equal to the time 203. This time period 202 varies according to the powder flow rate selected. The longer solenoid valve 116 is releasing pressure from the area above particle level 150, the less particles flow. The particles do not flow down through orifice member 110 as long as solenoid valve 116 is open for time 202, and it is during the time 116 is closed and abrasive pinch valve 128 is open, that powder will flow. The flow will continue until the end of time 203.

For example, if pinch valve 128 opens for 220 milliseconds (ms)(time 203) and solenoid valve 116 opens for 220 ms (time 202), no particles will flow. If pinch valve 128 opens for 220 ms and solenoid valve 116 opens for 90 ms, there will be 130 ms of particle flow. There is no particle flow when pinch valve 128 is OFF. The flow of abrasive particles are controlled by the timing of pinch valve 128 and solenoid valve 116. Particles flow when pinch valve 128 is open and solenoid valve 116 is closed.

The reason the particles flow is that the stream of particles and carrier gas goes from an area of high pressure to an area of low pressure, striving to achieve an equalization to the pressure chosen by the user for the particle stream emitting from the handpiece 130 through nozzle means 141. Particles flow when the pressure below the orifice member 110 is below the pressure above the powder level 150. As long as solenoid valve 116 is open, the pressure above particle level 150 is less than the pressure in the mixing chamber 111. This causes the air to flow up through the orifice member 110, through the powder level 150, and into the container 108. Thus there is no flow of particles to the handpiece 130 as indicated by time period 202. At the end of time 202, solenoid valve 116 closes. During this time, and because there is no equalization means in this device, the pressure at the top of the powder level 150 in the container is higher than the pressure in the mixing chamber 111 below orifice member 110.

The ON/OFF times that are used in the particle feed system described herein may vary greatly. These ON/OFF times represent a pulse of the system. The ON/OFF times may vary from 1 millisecond to 2000 milliseconds (2 seconds). The ON/OFF times are set by the manufacturer and determined by the electronic control module 101.

Among other factors, the ON/OFF timings are determined by the manufacturer according to the length of the various internal and external hoses in the unit, the diameters of these hoses, the fittings, and the like. The ON/OFF timings are set by the manufacturer using these factors to optimize the unit's performance.

In FIG. 2, the break lines to the right of time period 205 indicate that the ON/OFF sequence occurs many times.

Time period 205 is on the order of milliseconds. In typical operations of a air abrasion dental instrument, 205 repeats from two to four times per second while the instrument is operating.

The particles are forced through a plurality of holes in the orifice member 110. The number of holes in the orifice member is dependent on the amount and type of abrasive material used. In a preferred embodiment, the holes each have a diameter of about 0.015 inch and are used in a dental instrument. The diameter of the holes in the orifice member may range from about 0.010 to about 0.020 inch. For air abrasion dental instruments using the instant feed system, the holes may number from three to eight. A preferred number of holes for particle feed through the orifice member is four.

When the user deactivates the activation switch 132 the abrasive pinch valve solenoid 118 stops pulsing and receives no signal via path 119. This closes the abrasive pinch valve 128 and stops flow through air line 112. The solenoid valve 116 is activated to stop air flow from the particle container 108 at the same time that the abrasive pinch valve 128 closes. The solenoid valve 120 deactivates, opening the pinch valve 124. By opening pinch valve 124, any residual pressure and particles in the handpiece hose 129 and handpiece 130 are released through air line 125, through pinch valve 124, through air line 126, and into the exhaust chamber 127.

SECOND PREFERRED EMBODIMENT: ADVANCED DENTAL INSTRUMENT

The second preferred embodiment of the present invention is an advanced dental instrument. This instrument is equipped with a microprocessor in electronic control module 101. The microprocessor provides digital control signals and is programmed in accordance with conventional programming techniques.

A preferred microprocessor is manufactured by Microchip Technology and is identified as PIC 16C74A. This invention will operate satisfactorily with any similar microprocessor tool commercially available. A particular advantage of using a microprocessor in control module 101 to control the dental instrument equipped with the instant feed system is that it may be readily repaired, replaced, or upgraded as desired.

The unit's microprocessor will automatically adjust the beam intensity according to the selections indicated by the user. Beam intensity of the advanced dental instrument is defined as the amount of abrasive particles in the stream. The flow rate of the abrasive stream can vary from about 1 to about 20 grams per minute over a range of pressures from about 30 to about 160 pounds per square inch.

Microprocessor control allows particle flow rates to be selected precisely. Each setting is optimized according to the nozzle tip size, pressure setting, and amount of abrasive material in the container. The microprocessor can use data, previously collected in hardware testing, to create and utilize a look-up table of optimal settings.

When beginning operation of the air abrasion dental instrument of this invention, the unit is turned on by the toggle switch 138. The beam intensity indicator 411 and the standby 413b indicators will be lit. The unit is in "Standby" mode.

When in "Standby" mode, activation switch activity is disabled. Solenoid 116 depressurizes the container through porous filter 109, path 113, filter 114, and path 115. Beam intensity is selected by the user and may be further adjusted as described above.

The "Ready" mode is selected by button 414 and indicated by light 413a. Ready mode engages the main air solenoid valve 106, pressurize the system and allows activation switch operation. When the "Ready" mode is selected, the main air solenoid 106 allows air to flow through path 134, through one-way check valve 107 and path 135 to the container 108. When the activation switch 132 is depressed, the abrasive pinch valve 128 is opened. In this invention, activation is accomplished by the user depressing a foot switch 132 or pushing a switch in the handpiece 130. This opens the path for flow of particles from the container member 108 to the nozzle 141.

Specific operation of the instrument's particle feed has been described in detail previously. FIG. 1 and FIG. 2 combine to display the operating parts of the instrument and how abrasive pinch valve 128 and solenoid valve 116 alternate ON/OFF to start and stop flow as determined by electronic control module 101. In the advanced dental instrument of this invention, the electronic control module contains a microprocessor.

The fluid requirements for both dental units of this invention include an absolute maximum input pressure of 160 psi. The preferred maximum working pressure for the unit is 120 psi. Higher pressures may be achieved by simple changes to the pressure ratings of selected components. Such modifications are intended to be in the scope of the present invention.

The input gas must be clean and free of moisture. If the gas used is air, its source may be standard dental operatory compressed air system. The air used for this basic air abrasion unit must be clean and dry. Alternately, the air may be from a dedicated source of air as used by other air abrasion system. Any moisture or oil in the air supply will adversely affect the performance of the unit.

The dental instruments of this invention include an in-line coalescing filter element 163. This filter element removes more than 99% of water and oil vapor from the incoming air stream.

The unit will operate in an ambient temperature range from between +10 degrees C. to +40 degrees C. It will operate in the relative humidity range of 30% to 75%. Satisfactory atmospheric pressures range from 700 hPa to 1060 hPa. The units will not overbalance during normal operation, and are tested with a tilt angle of about 10 degrees. It is also designed to withstand falls from a height of one meter.

Sterilization of the cutting handpiece and nozzles can be accomplished by utilizing any conventional dental autoclave. The handpiece and nozzles are fully autoclavable by dry heat or steam. This is recommended prior to each use to ensure that the handpiece and nozzles cannot become a source of cross contamination of disease or infection.

When in use, the handpiece should be directed precisely at surfaces and tooth structures that are to be modified or removed. As in other dental air abrasion units, the nozzle cuts only directly from the nozzle tip or is 'end' cutting. 'Side' cutting, as practiced in high speed drilling with a burr, is not practiced.

The advanced dental unit may utilize any available nozzle tips that are sold by Kreativ, Inc., Among these are the supersonic nozzles manufactured by Kreativ, patent application Ser. No. 08/821,976, filed Mar. 13, 1997. The supersonic nozzles produce supersonic fluid velocities substantially above Mach 1 in a dental instrument using pressurized air and a temperature comfortable to the patient.

Both dental units are used for cavity preparation in classes I–VI. Both are lightweight and portable, weighing less than 15 pounds and can fit on a tabletop. The total space required for the unit is not more than one cubic foot. It may be a component of a modern air abrasion dental instrument which has stackable modules may include a variety of dental instruments.

More specifically, the air abrasion dental instrument which utilizes the particle feed system of the present invention may be part of a dental control unit. The dental control unit may hold other dental instruments such as a high speed handpiece, a low speed handpiece, an air/water syringe, an ultrasonic scaler, air compressors, curing lights and the like.

THIRD PREFERRED EMBODIMENT: BASIC DENTAL INSTRUMENT

Figure 3A:
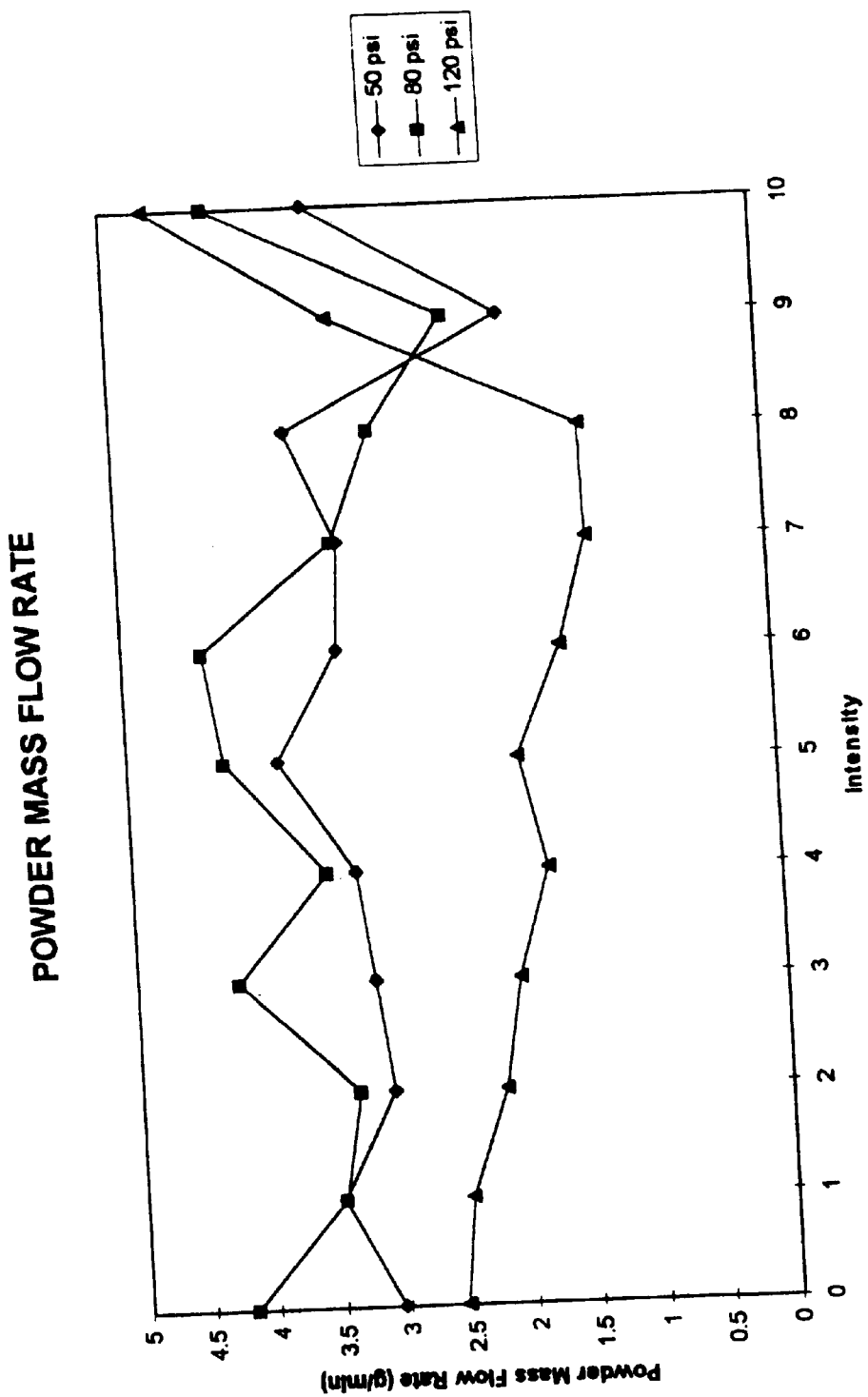
FIG. 3a is a graph of non-linear particle flow of a prior art air abrasion instrument.

The procedures recited above for the advanced dental unit and following the operational diagram of FIG. 1 also apply to a basic air abrasion dental instrument. A difference between the two is that the basic unit uses a circuit board and discrete logic in electronic control module 101 instead of a microprocessor. The basic air abrasion dental unit of this invention has particle flow settings which are factory set and based on an optimal air pressure range. The optimal air pressures are factory set in the range of about 60–80 psi. Although in the basic unit, the optimization of fluid flow is not customized by the electronics for each individual particle flow setting, the flow of abrasive is more linear than the particle feed of prior art air abrasion dental units. This linearity is demonstrated in FIG. 3b which shows the mass flow rate of abrasive particles at various particle energies. FIG. 3a shows the non-linear mass flow at various particle energies of a prior art systems with vibrator and equalization means.

The basic air abrasion dental instrument that uses the particle feed system of this invention operates with a single pulse timing operating mode. The beam intensity selections determine the particle flow rates of the air abrasion dental instruments. They may be selected by the user from the settings of low, medium, and high. Each of the beam intensities will vary in linear fashion, with a steady, even increase in the amount of abrasive material delivered to the handpiece. One of these settings is selected by pressing button 412.

For the basic unit, the low setting particle flow rate is from about 1 to about 3 grams/minute. The medium setting indicates a flow rate of from about 4 to about 6 grams/minute. Lastly, the high setting indicates a particle flow rate of from about 7 to about 10 grams/minute. These settings are based on the pre-set optimal factory settings for the basic air abrasion dental unit using the instant particle feed system.

The amount of particle flow may manually be 'fine-tuned' by adjusting pressure regulator 102. Air pressure adjustments, shown by the particle energy indicators 410 will be illuminated, indicating the air pressure that is in effect. Air pressure adjustments will determine the speed of the abrasive particles. A display of particle speed and the amount of abrasive particles fed in the dental instrument of this invention are pictured in FIG. 3b.

Other nozzles manufactured and sold by Kreativ, Inc. are enumerated in patent application Ser. No. 08/975,438 filed Nov. 21, 1997. These nozzles vary in size. The nozzles may be selected for particular dental procedures including a 0.018 inch diameter nozzle to remove large lesions and existing restorations, a 0.014 inch diameter nozzle for most small lesions, a 0.011 inch diameter nozzle for very precise cutting, diagnosis of occlusal pits and fissures, incipient Class II and III lesions or for placing fine retention in Class IV and V restorations.

The handpiece supplied with the basic unit may be fitted with one of a plurality of nozzles suitable for use with the unit. Recommended nozzles may be classified as small, medium, and large. The smallest nozzles have an internal tip diameter of about 0.011 inch. The small nozzles are generally used for precise dental cutting operations such as very precise cutting, diagnosis of occlusal pits and fissures, incipient Class II and III lesions or for placing fine retention in Class IV and VI restorations and a variety of minimally invasive dental procedures.

Medium-sized nozzles are those possessing internal tip diameters of 0.014 or 0.018 inch. These nozzles are used for moderate sized caries removal and cavity preparation. The medium sized nozzle tips are often used for cleaning and stain removal of the teeth.

The larger size nozzle tips are used for more aggressive procedures since they cut a wider path. The largest nozzles may have an internal diameter tip size of 0.026 inch. The larger tips are useful for large caries removal, amalgam removal, extra-oral microetching. The tips have angles at 90, 67, or 45 degrees.

Specific operation of the instrument's particle feed has been described in detail previously. FIG. 1 and FIG. 2 combine to display the operating parts of the instrument and how abrasive pinch valve 128 and solenoid valve 116 alternate ON/OFF to start and stop flow as determined by electronic control module 101. In the advanced dental instrument of this invention, the electronic control module contains a microprocessor.

COMPARATIVE FIGURES A–D

Comparative Figure A: from U.S. Pat. No. 2,696,049 to Black

Earlier air abrasion instruments had different particle feed systems. In U.S. Pat. No. 2,696,049 Black describes a method where particles are fed into a stream of gas to provide a stream of dental air abrasive to treat teeth. Comparative Figure A shows the arrangement of the hopper and vibrator that comprise the feed system of the '049 patent.

This patent teaches feeding the particles from a hopper type of abrasive container 10 which is bolted to a vibrator platform 31. The vibrator imparts motion imparted that has both vertical and horizontal components. In operation, the electromagnet 44 pulls the platform 31 downwardly and backwardly. The springs 35 and 36 return it upwardly and forwardly.

The vibratory motion causes particles lying on the orifice plate 23 to pass over the orifice holes 25. Since the abrasive particle size is smaller than the diameter of the orifice, there will be a steady feeding of particles through the openings into the mixing chamber 11 where they are entrained into the gas stream and discharged through the conduit 12. The gas swirls through the mixing chamber picking up the powder on its way as long as the vibration continues. As soon as the vibration stops, the feed of abrasive particles into the mixing chamber stops even though gas may flow therethrough.

Comparative Figure B: from U.S. Pat. No. 5,525,058 to Gallant et al

U.S. Pat. No. 5,525,058 illustrates another vibratory feed system for an air abrasion dental systems. Comparative Figure B illustrates the advancement of particulate material upwardly within spiral groove 180 through duct 181 where it enters resilient, flexible tubing 182 and exit means 183. From here the abrasive particles exit container 175 and passes through means 184 to join conduit 195 (not shown).

As shown by Comparative Figure B, the abrasive delivery system 105 includes a sealed lower chamber 175 mounted on a base 176 and an abrasive supply vessel 177 which is bolted or otherwise fastened to the top of the canister member 175. Located within chamber 175 is an upwardly open cylindrical particle feed receptacle 178 which is mounted on a vibratory device 179.

The vibratory device 179 is electrically operated. The rate of vibratory feed is controlled by a preset adjustable control device 190 mounted on the equipment control panel (not shown). Device 190 may be set manually by the operator or it may function as a pressure-responsive device which automatically adjusts through via connections to switch 191 (not shown) so that an appropriate rate is provided for the selected operating pressure level.

Comparative Figure C: from U.S. Pat. No. 5,618,177 to Abbott

U.S. Pat. No. 5,618,177 illustrates still another arrangement for feeding pressurized particulate material from a storage member to a handpiece for performing air abrasion dentistry. Comparative Figure C illustrates a preferred embodiment of the pressurization and feeding arrangement according to the '177 invention.

The feeder 12 includes a funnel-shaped hopper 50 that is suspended by an elastic member 52. A vibrator 72 oscillates the bottom end of the hopper. These vibrations are transferred to the hopper via a flexible diaphragm assembly 66. The hopper 50 is thus subjected to primary vibration forces and torque. These forces induce the abrasive particles in the hopper 50 to fluidise thoroughly. Abrasive particles are drawn, largely by gravity, down into the inlet nozzle 70. Here it is caught by the pressurized propellant gas delivered through the pressure inlet means 17. In this manner, the abrasive particles are forced out through outlet means 20.

Comparative Figure D: from U.S. Pat. No. 5,718,581 to Fernwood et al

U.S. Pat. No. 5,718,581 illustrates yet another arrangement for feeding pressurized particulate material from a storage member to a handpiece for performing air abrasion dentistry. With reference to Comparative Figure D, a container is shown for holding abrasive particles and a vibrating means. More specifically, Comparative Figure D depicts the container interior 12 containing abrasive particles 15 and pressurized air from the air inlet 10.

It also may be seen from Comparative Figure D that the device 20 is attached to an assembly 32 for producing vibrations within the mass of flowable particles 15. The vibration-producing assembly 32 is designed to produce vibrations that are distributed throughout the mass of flowable particles 15 are removed from the interior 12 of container 11 through screen 30 and inlet means 26.

DIFFERENCES BETWEEN THE INSTANT INVENTION AND THE PRIOR ART

The feed system of the instant invention differs from the Comparative Figures A–D in several ways. The first differentiating aspect of the instant feed system is that it has no vibrator. The feed systems of each of the above comparative devices all use vibration devices. More specifically, Comparative Figure A from U.S. Pat. No. 2,696,049 features a vibrating platform 31.

Comparative Figure B from U.S. Pat. No. 5,525,058 illustrates a vibrating device 179. A further difference of '058 is that it operates with a mixture of particles and air being forced upward under pressure with vibrational activity or propagation, against gravity, through a helical means. This feature distinguishes the '058 patent from both the other prior art feed systems and the instant feed system.

Comparative Figure C from U.S. Pat. No. 5,618,177 illustrates a vibrator 72 that oscillates the bottom end of a hopper. These vibrations are transferred to the hopper which is subjected to primary vibration forces and torque. Abrasive particles are fluidized and drawn, largely by gravity, down into the inlet nozzle. From here it is caught by the pressurized propellant gas and eventually delivered and forced out through outlet means.

Comparative Figure D from U.S. Pat. No. 5,718,581 also teaches a vibration-producing assembly which vibrations are distributed throughout the mass of flowable particles. In the '581 patent, the vibrator assembly in combination with the vibration transmitter maintains the favorable flow of particles under gravity feed. The particle feed system of '581 uses both gravity feed and oscillation in its arrangement for feeding pressurized particulate material.

A second differentiating aspect of the instant particle feed system is the lack of a pressure equalizing member. In Comparative Figure A, the gas entering through conduit 9 is under considerable pressure. To equalize this pressure throughout the particle container and mixing chamber is provided a balancing means 28.

Comparative Figure B from U.S. Pat. No. 5,525,058 describes a branch conduit 188 which supplies air at the same pressure to the abrasive particle supply chamber 177 by means of a connection 189 (not shown) which communicates with the interior of the supply chamber 177.

Comparative Figure C from U.S. Pat. No. 5,618,177 mentions filtered opening fittings 60 and 62 preferably extending through a wall 30 above and below the upper edge of the funnel, 50. These fittings are then connected by external tubing 64 to equalize the pressure on either side of the funnel.

The instant system has no pressure equalization means of any kind. The instant air abrasion dental instrument employs differential, synchronous pulse width modulated pressure regulation. There cannot be pressure equalization means in the current particle feed system. The instant particle feed system operates by controlling the differential pressure above the particle level 150 in the container and the pressure in the mixing chamber 111 below the orifice member 110.

Figure 3B:
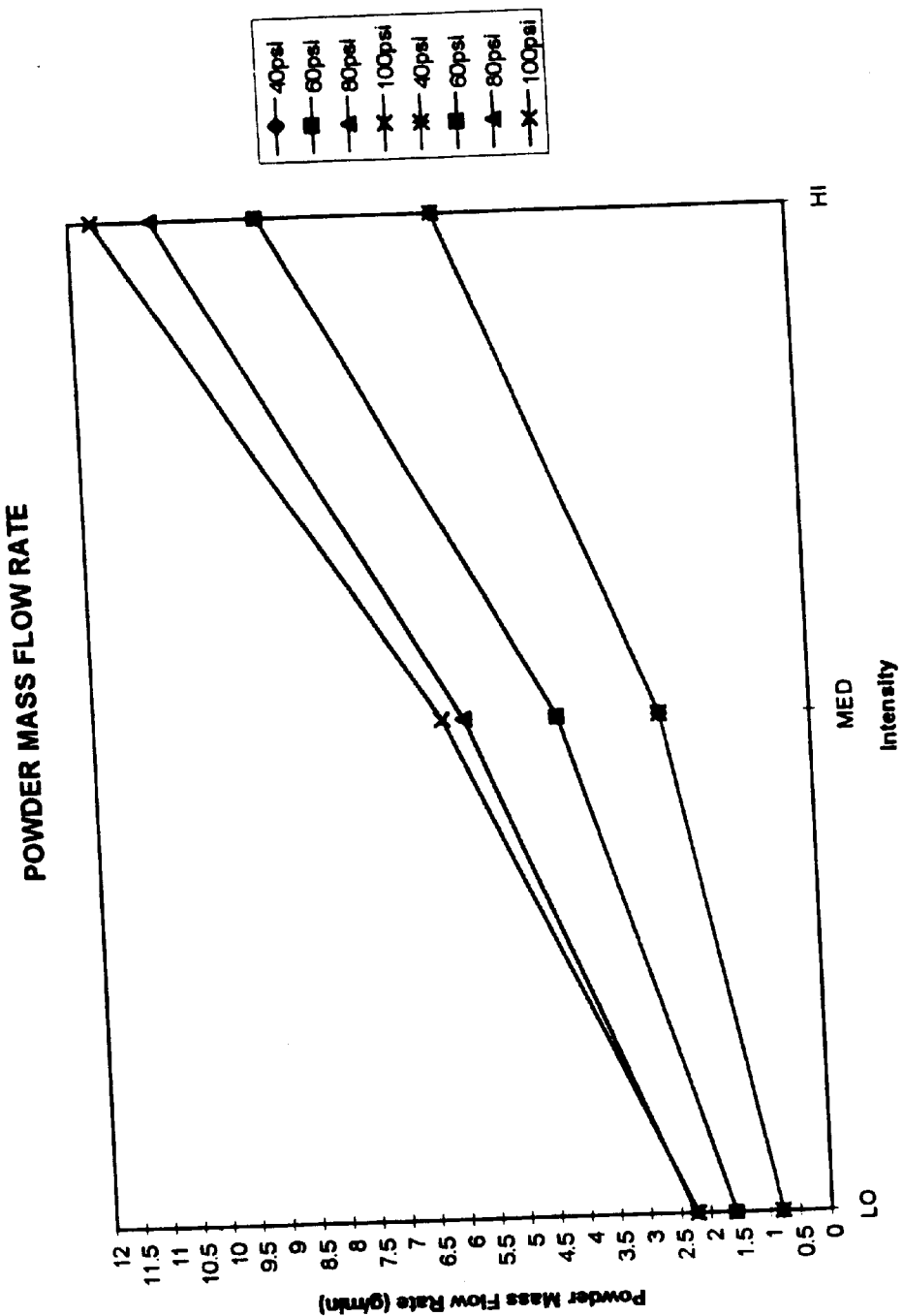
FIG. 3b is a graph of linear particle flow of this invention.

A third differentiation between the instant invention and the particle feed systems shown and described in Comparative Figures A–D is the ability or the instant feed system to have separate controls for the beam intensity and the particle energy of the particle feed. As shown in FIG. 3b, the amount of particle flow can be determined by either adjusting the beam intensity or the particle energy (30–160 psi). As seen in FIG. 3b, the user can select a desired mass flow rate by adjusting either the beam intensity or particle energy that corresponds to the desired mass flow rate.

For example, if the user desires a particle mass flow rate of about 5 grams/minute, he may select the 'medium' beam intensity and a particle energy of 80 psi as shown in FIG. 3b. He may also select the 'hi' beam intensity and a particle energy of 40 psi. As shown in the graph that is FIG. 3b, about the same amount of abrasive will be delivered from the handpiece for both of these sets of conditions.

FIG. 3b also shows the linearity of the particle flow rate with intensity. As has been stated, linear particle flow means that abrasive delivered by the unit varies in direct proportion to the beam intensity. The graph in FIG. 3b shows lines with quite even, constant slopes that confirm the regular, constant particle mass flow rates. In contrast, FIG. 3a shows a more irregular, erratic plot of particle mass flow rate and beam intensity resulting from a prior art air abrasion dental instrument. The instrument used for comparative purposes was the Kreativ unit, described in pending application Ser. No. 08/975,438. In contrast to the instant invention, the slopes of the lines in FIG. 3a are non-linear. It is only at the higher pressures (80 psi or greater) that the slope of the lines are linear.

In the air abrasion devices shown in Comparative Figures A–D, the amount of powder fed is determined by the air pressure selected. This is an additional contrast to the separation of these two operating characteristics of the instant invention.

Although the present invention has been demonstrated in dental applications, it is applicable to other industries as well. For example, in the metal finishing industry, the feed system of this invention may find use in removing coatings from a metal surface prior to re-application of coating to the metal surface. In the sand blasting industry, the abrasive particle feeding system of this invention may be used to clean stone or ceramic surfaces prior to application of protective coatings or for cleaning the surface. It is to be understood that the feed system of the instant invention may be modified for use in other industries that employ particle feeding to remove unwanted materials from a surface.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A particle feeding device comprising a container member adapted to hold abrasive particles, a mixing chamber in which a quantity of abrasive particles from said container member are combined with a carrier gas, and a substantially vibration-free pressure differential feed system that enables the delivery of a substantially linear flow of abrasive particles over a range of carrier gas pressures, said substantially vibration-free pressure differential system including a first valve disposed above the particle level in the mixing chamber and a second valve disposed beneath said mixing chamber wherein flow of abrasive particles is caused by a discontinuous gas pressure differential between the container member holding the abrasive particles and the mixing chamber, said device further including a control mechanism which controls the rapid opening and closing of at least one of said first and second valves to create said discontinuous gas pressure differential.

2. The particle feeding device of claim 1 including a handpiece from which a pressurized fluid stream laden with the abrasive particles is forced against a surface to remove unwanted material from the surface.

3. The particle feeding device of claim 1 wherein the gas pressure differential can be varied by said control mechanism in the range from about zero to about 100 psi.

4. The particle feeding device of claim 1 wherein the abrasive particles have an average size of about 27 to about 50 microns in diameter, said device further including an orifice member having a plurality of openings, each opening having a diameter in the range of from about 0.010 to 0.020 inch.

5. The particle feeding device of claim 1, wherein said control mechanism includes flow regulation means for regulating the flow rate of said abrasive stream so that a user may select one of a plurality of flow rates.

6. The particle feeding device of claim 1, wherein said control mechanism includes a microprocessor which controls the gas pressure differential between the container member and the mixing chamber.

7. The particle feeding device of claim 5, wherein the flow rate of abrasive particles from the container member can be varied by said flow regulating means over a range from a rate of from about 1 to about 20 grams per minute over a range of carrier gas pressures from about 30 to about 160 pounds per square inch.

8. The particle feeding device of claim 1, wherein the mixing chamber and the container member are separated by an orifice member having a plurality of openings sized to allow particles to pass therethrough and wherein the differential in pressure between an area above the level of particles in the container member and below the orifice member is synchronized with the opening and closing of said first and second valve members at a rate of greater than one open and close sequence per second which causes flow of abrasive particles to a handpiece when the device is activated by a user.

9. The particle feeding device of claim 8 where the abrasive particles flow as a pulsed stream in a plurality of pulsed operating modes.

10. The particle feeding device of claim 1, wherein said control mechanism includes a microprocessor having means in which a user can selectively adjust a desired particle flow rate, said adjusting means including a timing control which controls the particle flow rate based upon at least one of the parameters selected from the group consisting of gas pressure, the type of nozzle, a specified particle feed setting and amount of abrasive material in the container member.

11. The particle feeding device of claim 1, wherein said instrument is used as a dental air abrasion instrument to prepare teeth surfaces for various treatments.

12. The particle feeding device of claim 1, wherein the abrasive material is selected from at least one the group consisting of sodium bicarbonate, urea, dolomite, and aluminum oxide.

13. A particle feeding device comprising:

a canister member containing a quantity of abrasive particles a mixing chamber through which a pressurized stream of a carrier gas flows;

an orifice member having a plurality of openings through which abrasive particles pass into said mixing chamber from said container member;

a handpiece interconnected to and downstream of said mixing chamber;

a first valve member disposed between the handpiece and said mixing chamber; and a second valve member disposed above the level of abrasive particles in said canister member, wherein the simultaneous and rapid opening and closing of said first valve member and said second valve member creates a pressure differential between the abrasive level in the canister member and the mixing chamber, each of the open-close sequences drawing a controlled amount of abrasive particles out of the canister member and into the mixing chamber.

14. The particle feeding device of claim 13 wherein the abrasive particle stream is pulsed wherein said first valve member is opened for a first time period ranging from about 1 milliseconds to about 2000 milliseconds (2 seconds) and said second valve member is simultaneously opened for a second time period ranging from about 1 milliseconds to about 2000 milliseconds (2 seconds) and wherein subsequent valve opening and closing of said first and second valve members occur sequentially.

15. A particle feeding device comprising:
   a container member adapted to retain a supply of abrasive particles;
   a mixing chamber where a portion of the abrasive particles contained in the container member are combined with a flowing carrier gas; and
   a substantially vibration-free pressure differential feed system that enables the delivery of a substantially linear flow of abrasive particles over a range of carrier gas pressures to a connected handpiece,
   wherein particle flow from said container member to said mixing chamber is caused by a gas pressure differential induced therebetween,
   said device further including a control mechanism enabling a user to select one of a plurality of different particle flow rates.

16. The particle feeding device of claim 15, in which said control mechanism includes one of a circuit board having discrete logic and a microprocessor for opening and closing valves disposed above the top of the abrasive particle level in the container member and below the mixing chamber.

17. The particle feeding device of claim 16, in which the valves are continually opened and closed in a timed sequential fashion to produce a non-continuous pressure differential, resulting in substantially linear flow of abrasive particles from the handpiece.

18. The particle feeding device of claim 16, wherein the valves are continually opened and closed by the control mechanism according to preset time intervals wherein particles flow when the valve below the orifice plate is open and the valve above the particle level is closed.

19. The particle feeding device of claim 17, wherein the control mechanism includes means for varying the preset time intervals during which said valves are opened and closed so as to vary the flow rate of particles from the container member into the mixing chamber.

20. The particle feeding device of claim 15 wherein abrasive particles are used in dentistry to prepare teeth surfaces for various treatments.

21. An air abrasion dental instrument including:
   a handpiece from which a stream of abrasive particles is ejected;
   a nozzle connected to the handpiece which directs the stream of abrasive particles from the handpiece to teeth,
   a container member for holding a quantity of abrasive particles; and
   a substantially vibration-free pressure differential feed system for delivering a substantially linear flow of abrasive particles over a range of gas pressures, including:
   (a) a mixing chamber in which the abrasive particles from said container member are mixed with gas flowing therethrough,
   (b) a mechanism which controls the operation of valve members which rapidly open and close causing a difference in pressure levels, wherein said valve members includes a first valve member disposed above the abrasive particle level in the container member and a second valve member disposed below the mixing chamber,
   (c) a one-way check valve to control the direction of carrier gas flow within the instrument.

22. The air abrasion dental instrument of claim 21 including
   (a) a plurality of pinch valves which control the flow of abrasive particles from the canister member to the handpiece,
   (b) a plurality of solenoid valves which control the pinch valves; and
   (c) a one-way check valve to control the direction of air flow within the instrument.

23. The air abrasion dental instrument of claim 21 further including a display/control panel which enables operating mode selection by a user and displays the chosen selection to the user.

24. The air abrasion dental instrument of claim 21, wherein the control mechanism includes a microprocessor which controls the particle flow rate.

25. The air abrasion dental instrument of claim 21, including an in-line coalescing filter element which removes substantial quantities of water and oil vapor from the gas stream prior to entering said mixing chamber.

26. The air abrasion instrument of claim 21, in which the handpiece is part of a modular dental control which holds at least one other dental instrument from the group consisting of a high speed handpiece, a low speed handpiece, an air/water syringe, an ultrasonic scaler, air compressors, and a curing lamp.

27. The air abrasion dental instrument of claim 21 further including a regulator for controlling the amplitude of air pressure within the instrument.

28. The air abrasion dental instrument of claim 21 further including an activation switch to initiate abrasive particle flow of the instrument.

29. The air abrasion dental instrument of claim 23 wherein the display/control panel includes a plurality of beam intensity selections and a beam intensity selector member;
   a toggle member that allows the user to switch between ready and standby modes;
   a visual indicator displaying the operating mode selected;
   a plurality of carrier gas pressures that may be selected by a user, wherein the selected gas pressure determines the speed of the abrasive stream.

30. The air abrasion dental instrument of claim 21 wherein said control mechanism sequentially opens and closes each said first and second valve members in a predetermined time sequence in which said first valve member is opened for a first time interval and said second through the handpiece in a pulsed particle stream.

31. The air abrasion dental instrument of claim 21 wherein said control mechanism sequentially opens and closes each said first and second valve members in a predetermined time sequence in which said first valve member is opened for a first time interval and said second valve member is simultaneously opened for a second time interval and particles flow from said container member to said mixing chamber when the second time interval is greater than the first time interval.

32. The air abrasion dental instrument of claim 21 wherein said first valve member and said second valve member open and close sequentially in rapid fashion such that particles flow when the gas pressure level is higher above the particle level in the container member than is the gas pressure below said mixing chamber.

33. The air abrasion dental instrument of claim 21 wherein the rapid opening and closing of said valve members eject a substantially linear pulsed stream of abrasive particles from said handpiece.

34. An air abrasion instrument including:
a handpiece from which a fluid stream of abrasive particles flows, and
a substantially vibration-free article feeding system for introducing particles into the fluid stream, the particle feeding system having a container section for holding a supply of abrasive particles in a container member and a mixing chamber through which a carrier gas passes to said handpiece,
the container member and mixing chamber being separated by an orifice member which prevents particles in the container member from flowing into the mixing chamber when the pressure in the container section is less than the pressure in the mixing chamber and
an electronically controlled valve mechanism for regulating the pressure differential between the container section and the mixing chamber, without vibration thereof.

35. The air abrasion instrument of claim 34, including an opening in the container section which allows the pressure in the container section to be reduced, a passageway between the mixing chamber and the handpiece through which the fluid stream flows and into which are mixed particles flowing from the mixing chamber due to the differential in pressure between the container, section and mixing chamber, and
wherein the electronically controlled valve mechanism includes a first valve member at the opening which is opened for a first duration as the particles are being fed into the fluid stream and a second valve member along the passageway which is opened for a second duration as the particles are being fed into the fluid stream, the first duration being shorter than the second duration.

36. The air abrasion instrument of claim 35, where the first and second duration is controlled so that the rate of feed of particles from said container member is about 1 to about 20 grams per minute.

37. The air abrasion instrument of claim 35, where the fluid stream exiting from the handpiece is pulsed.

38. The air abrasion instrument of claims 35, where gas under pressure flows through the orifice member in a first direction during a period of abrasive particle flow from said particle container member and in a second direction during a period of no abrasive particle flow.

39. An air abrasion instrument including
a handpiece from which a fluid stream of abrasive particles flows, and
a particle feeding system for introducing particles into the fluid stream, the particle feeding system having a container section for holding a supply of particles in a container member and a mixing chamber,
the container member and mixing chamber being separated by an orifice member which allows particles in the container member to flow into the mixing chamber when the pressure in the container section is higher than the pressure in the mixing chamber and fed through the handpiece, and
an electronically controlled valve mechanism for regulating the pressure differential between the container section and the mixing chamber.

40. A method of feeding abrasive particles from a feeding device to a handpiece wherein said feeding device includes a first valve member disposed above a quantity of abrasive particles stored in a particle container member and a second valve member disposed beneath a mixing chamber situated beneath said container member through which carrier gas passes, said method including the steps of:
opening said first valve member for a first predetermined time interval;
simultaneously opening said second valve member for a second predetermined time interval which is less than said first predetermined time interval to induce a pressure differential; and
causing the flow of abrasive particles from the container member to said mixing chamber.

41. The method of claim 40 including the additional steps of:
(a) rapidly opening and closing at least one said valve member so as to induce said pressure differential of said first and second valve members between a top and a bottom of said particle storage container member;
(b) varying said pressure differential to cause a discrete quantity of particles from said storage container member to enter and be mixed with carrier gas in said mixing member; and
(c) delivering a particle-laden stream to said handpiece.

42. The method of feeding abrasive particles of claim 40 wherein the sequential opening and closing of said second valve member produces a discontinuous abrasive particle stream which flows through the handpiece in a pulsed particle stream.

43. The method of feeding abrasive particle of claim 40 wherein stream of abrasive particles flowing from the container member can be varied from about 1 to about 20 grams per minute over a range of carrier gas pressures ranging from about 30 to about 160 pounds per square inch.

44. The method of feeding abrasive particle of claim 40 wherein stream of abrasive particles flowing from the container member can be varied from about 1 to about 20 grams per minute over a range of carrier gas pressures ranging from about 30 to about 160 pounds per square inch.

* * * * *

UNITED STATES PATENT AND TRADEMARK OFFICE
CERTIFICATE OF CORRECTION

PATENT NO.    : 6,083,001
DATED         : July 4, 2000
INVENTOR(S)   : Deardon, JD et al.

Page 1 of 1

It is certified that error appears in the above-identified patent and that said Letters Patent is hereby corrected as shown below:

<u>In Claim 32,</u>
Line 6, change 'below said mixing chamber' to 'in said mixing chamber'.

<u>In Claim 34,</u>
Line 4, change 'article' to 'particle'

Signed and Sealed this

Third Day of July, 2001

*Attest:*

NICHOLAS P. GODICI
*Attesting Officer*    *Acting Director of the United States Patent and Trademark Office*